United States Patent [19]
Hussein et al.

[11] Patent Number: 5,190,538
[45] Date of Patent: Mar. 2, 1993

[54] METHOD AND APPARATUS FOR SUBJECTING A BODY SITE TO A MOVABLE BEAM OF LATERALLY DIRECTED LASER RADIATION

[75] Inventors: Hany M. G. Hussein, Costa Mesa; Vahid Saadatmanesh, Irvine; Stanislaw Sulek, Huntington Beach, all of Calif.

[73] Assignee: Trimedyne, Inc., Irvine, Calif.

[21] Appl. No.: 689,455

[22] Filed: Apr. 22, 1991

[51] Int. Cl.⁵ .............................................. A61B 17/36
[52] U.S. Cl. .......................................... 606/17; 606/7; 606/15; 606/16
[58] Field of Search .................. 606/17, 18, 13, 19, 606/15, 16, 7; 128/395–398

[56] References Cited

U.S. PATENT DOCUMENTS

| | | | |
|---|---|---|---|
| 4,445,892 | 5/1984 | Hussein et al. | 606/15 X |
| 4,648,892 | 3/1987 | Kittrell et al. | 606/18 X |
| 4,672,961 | 6/1987 | Davies | 606/18 X |
| 4,768,858 | 9/1988 | Hussein | 606/7 X |
| 4,852,567 | 8/1989 | Sinofsky | 606/16 X |
| 4,994,060 | 2/1991 | Rink et al. | 606/7 X |
| 5,029,588 | 7/1991 | Yock et al. | 606/18 X |

*Primary Examiner*—Peter A. Aschenbrenner
*Attorney, Agent, or Firm*—Dressler, Goldsmith, Shore, Sutker & Milnamow, Ltd.

[57] ABSTRACT

A method and device are provided for directing laser radiation to a body cavity site. A hollow, elongate, optical fiber is advanced to the vicinity of the site and coupled to a laser source with a distal end region of the fiber extending along a longitudinal axis. The fiber terminates in a transverse, substantially flat, annular, energy delivery surface for emitting laser radiation transmitted by the fiber generally parallel to the axis. The radiation is intercepted axially adjacent the energy delivery surface and is reflected in a beam radiating substantially transversely of, and substantially around, the axis. A reflector block is provided for reflecting the radiation and is connected to an actuator for locating the reflector block at selected axial positions along the axis whereby the beam irradiates the body site along the axis.

4 Claims, 2 Drawing Sheets

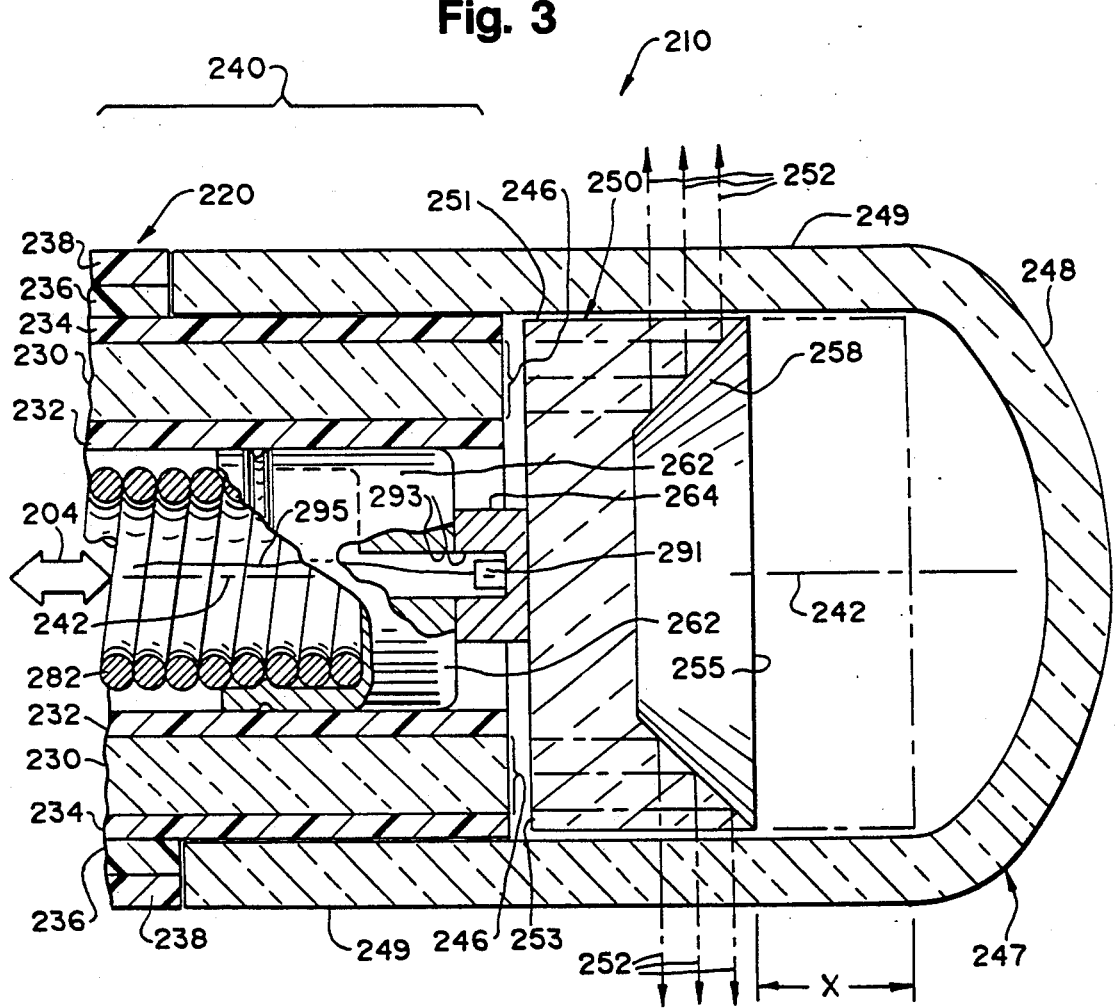

METHOD AND APPARATUS FOR SUBJECTING A BODY SITE TO A MOVABLE BEAM OF LATERALLY DIRECTED LASER RADIATION

TECHNICAL FIELD

The present invention relates to medical devices and procedures which employ laser energy transmitted through an optical fiber to a site in a patient's body.

BACKGROUND OF THE INVENTION AND TECHNICAL PROBLEMS POSED BY THE PRIOR ART

A variety of instruments have been provided or proposed in recent years for applying laser radiation to internal body sites. Such instruments typically include a relatively small diameter, elongated, radiation transmitting flexible member or fiber. Typically, the fiber is advanced through an endoscope or other surgical tool into a body cavity, artery, or other body passage to a selected internal treatment location.

Instruments of the above described type may be broadly defined as laser catheters. As used in this specification and in the claims, the term "laser catheter" or "catheter" is intended to broadly include a flexible, or even rigid, instrument for being inserted into a natural or surgically created internal passage or cavity in a body and through which laser energy is transmitted.

A number of designs have been proposed for a laser catheter which can be inserted into a body passage and operated to direct the laser radiation laterally in a 360° beam to the surrounding site in the body cavity. For example, U.S. Pat. No. 4,672,961 discloses a device in which a special, parabolic reflecting surface is employed in conjunction with a plurality of circumferentially spaced optical fibers mounted in a template around a guiding tube, and this assembly is carried within a surrounding tube that slides within a fixed outer tube.

U.S. Pat. No. 4,852,567 discloses a laser tipped catheter in which laser radiation is radially directed by employing a defusing tip on a tapered optical fiber or by employing a conical reflecting surface disposed in the beam path of a plurality of circumferentially spaced optical fibers.

U.S. Pat. No. 4,799,479 discloses a type of laser catheter in which the cladding is removed from an area along the optical fiber and in which the optical fiber core is abraded so that the fiber surface is roughened. This effects a lateral diffusion of the laser radiation.

While the above-discussed designs may function to radiate laser radiation generally transversely of the longitudinal fiber axis, it would be desirable to provide an improved device which more accurately controls the radiation beam and yet does not require special modifications to an optical fiber or complex arrangements of multiple optical fibers.

It would also be advantageous if such an improved device could efficiently transmit the radiation laterally with a minimum of dispersion, attenuation, or other radiation beam losses.

Some designs employ an internally reflecting prism for directing the radiation laterally. See, for example, U.S. Pat. Nos. 4,445,892 and 4,740,047. U.S. Pat. No. 4,445,892 also discloses, as does U.S. Pat. No. 4,785,815 and published PCT application No. PCT/US89/02492, a design for a laser catheter wherein the radiation is reflected laterally by a mirror. In the design disclosed in the U.S. Pat. No. 4,445,892, the optic system can be rotated with respect to the longitudinal axis so as to sweep through a 360° arc. The mirror can also be pivoted on a ball-and-socket joint by means of guide wires. While this design can be effective in applications for which it is intended, it would be desirable to provide an improved laser catheter device which could be efficiently employed in a variety of medical procedures.

In particular, it would be beneficial if such an improved device could provide radiation in a 360° beam via a relatively simple transmission system. It would also be advantageous if such a 360° beam could be moved along the axis of the catheter wile the catheter remains stationary within the body cavity so as to minimize tissue trauma while at the same time permitting irradiation of a selected length of the surrounding body cavity tissue.

Finally, designs have been proposed for incorporating a hollow optic fiber (i.e., a fiber having a tubular configuration) in a medical device in which a wire can be disposed within the central channel of the fiber to allow axial movement of the wire for performing a pre-defined function at the distal end of the fiber. See for example, U.S. Pat. Nos. 4,768,858 and 4,799,479. Although these designs may take advantage of the central channel of the hollow optic fiber, it would be desirable to incorporate a hollow optic fiber in an improved design wherein laser radiant energy can be efficiently directed substantially transversely of the longitudinal axis and wherein a selected site can be efficiently irradiated along the axis.

The present invention provides an improved laser radiation delivery method and catheter suitable for coupling to a laser source to direct radiant laser energy laterally to a selected body cavity site, and the invention can accommodate designs having the above-discussed benefits and features.

SUMMARY OF THE INVENTION

The present invention is eminently suitable for embodiment in a medical device for laterally directing radiant energy to a selected body site in a controlled manner for performing a medical procedure, and the present invention includes a method for so directing such energy.

The method and device of the present invention may be employed to transmit radiant laser energy along a body site without requiring movement of the device in contact with the body tissue at the site. This can, of course, eliminate, or at least reduce, the potential for trauma to the site. Additionally, the improved method and device of the present invention can permit a more accurate control of the delivery of the radiation along the body site.

The method and device of the present invention are effective without requiring a plurality of optic fibers or without requiring rotation of mechanical elements at the body site—thus simplifying the invention procedure and device components.

In accordance with the invention, laser energy is transmitted along a hollow optic fiber and is emitted at the distal end of the optic fiber substantially transversely of the longitudinal axis of the optic fiber.

A method aspect of this invention contemplates the introduction of a catheter into, for example, a body lumen or other cavity (natural or surgically created). The catheter includes the hollow, elongate, optical fiber. The fiber is advanced to the vicinity of the selected body site, and the fiber is coupled to a laser source. The distal end region of the fiber extends along a longitudinal axis at the body site. The laser radiation is transmitted through the length of the fiber and is emitted from a substantially flat, annular, energy delivery surface at the end of the fiber.

The laser radiation is intercepted axially adjacent the energy delivery surface and is reflected in a beam that radiates outwardly, around the axis. At least a portion of the beam is radiated substantially transversely of, and substantially 360° around, the axis. The interception and reflection of the radiation is effected at selected axial positions along the longitudinal axis relative to the energy delivery surface whereby the beam irradiates a selected body site along the axis. In one preferred method of operation, a reflecting surface adjacent the energy delivery surface is moved continuously between a position closest to the energy delivery surface and a position further from the energy delivery surface.

The catheter of the present invention permits placement of the catheter under direct vision, or by means of fluoroscopy or ultrasound. The device is especially suitable for use in prostatic resection or endometrial (uterine) ablation. Once the device is in place, it is easily operated (e.g., for about 4 minutes at 60 watts power when used for prostatic resection).

In accordance with an apparatus aspect of this invention, the catheter includes the above-described hollow, elongate, optical fiber in a form adapted for coupling to the laser source.

A reflector means is positioned axially adjacent the energy delivery surface for intercepting and reflecting the emitted radiation in a beam radiating substantially transversely of, and substantially around, the axis. In one embodiment, the reflector means includes a conical or frustoconical mirror surface. The apex of the conical or frustoconical surface is pointed toward the distal end region of the optic fiber, and the central axis of the reflecting surface is substantially aligned with the longitudinal axis of the distal end region of the optic fiber.

In another embodiment, the reflector means includes a block of laser transmissible material of a composition through which the radiation can be transmitted. The block has a cylindrical side surface defined between first and second ends around a central axis that is generally coincident with the longitudinal axis of the fiber distal end region.

The first end of the reflector block faces the energy delivery surface of the fiber and defines a generally flat, circular, end surface substantially parallel to the energy delivery surface. The second end of the reflector block has a recess defined by a frustoconical surface around the central axis.

The reflector block and external region adjacent the frustoconical surface have predetermined indices of refraction. Radiation emitted from the fiber energy delivery surface passes into the block wherein substantially all of the radiation is internally reflected by the frustoconical surface and passes out of the block through the cylindrical side surface to the body site.

The reflector means, whether it is an externally reflecting mirror or a laser energy transmissible block with an internally reflecting surface, is connected to an actuator means. The actuator means locates the reflector means at selected axial positions along the longitudinal axis of the distal end region of the fiber. In a preferred embodiment, the actuator means includes a flexible drive cable disposed within the central opening of the hollow fiber. The flexible drive cable is adapted for axial movement relative to the fiber to control movement of the reflector means.

The novel radiation transmitting method and catheter device of the present invention may be efficiently employed with a hollow optic fiber. The fiber may be maintained stationary within the body cavity with the distal end adjacent the selected body site. The other catheter portions in contact with the body tissue are similarly maintained stationary during the irradiation of the body site. Movement of the reflector means axially along the end of the catheter can be effected without the body tissue being engaged by any moving parts. Accordingly, the potential for trauma is eliminated or at least substantially reduced.

The catheter can be provided with a suitable cap or cover at the distal end for sealing the device off from body fluids and for containing a particular environment within the catheter.

The catheter may employ various types of laser energy. The laser radiation may be suitably produced by a conventional laser and may include infrared radiation (IR) and ultraviolet radiation (UV), as well as visible laser light. Examples of laser types that can produce suitable energies include: carbon dioxide, argon, holmium: yttrium aluminum garnet (holmium: YAG), neodymium: yttrium aluminum garnet (Nd:YAG), and excimer. The device is very effective in providing radiant energy for a range of laser radiation frequencies and types, particularly when the reflector means of the device is provided with a reflective surface of a suitable dielectric material or a metal coating of gold, copper, silver, platinum, or the like.

The present invention can also be embodied in designs which employ a thermocouple or other thermal sensing means for detecting excessive heating of the reflector means which could occur in some circumstances (e.g., tissue adherence to the reflector means or excessively long periods of laser operation). The thermocouple can be provided as part of a control system for reducing or terminating the emission of the laser radiation in such circumstances.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 3 is a view similar to FIG. 1 but showing a second embodiment of the catheter.

DESCRIPTION OF THE PREFERRED EMBODIMENTS

The apparatus of the present invention is embodied in a medical device for applying radiant laser energy laterally to a selected body site in an efficient manner that substantially eliminates or reduces trauma to the site while still permitting a radiation beam to be moved along the longitudinal axis of the catheter. The apparatus incorporates a single optic fiber to thereby reduce the complexity found in some prior art designs.

The device of the present invention can be operated to irradiate the body site with a 360° laser energy beam of a desired intensity. This beam can be used in a variety of medical procedures for effecting coagulation, ablation, vaporization, cutting, and the like.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

The apparatus of this invention may be employed with a suitable conventional laser and coupling system therefor, the details of which, although not fully illustrated or described, will be apparent to those having skill in the art and an understanding of the necessary functions of such devices. The detailed descriptions of such devices are not necessary to an understanding of the invention and are not herein presented because such devices form no part of the present invention.

Figure 1:
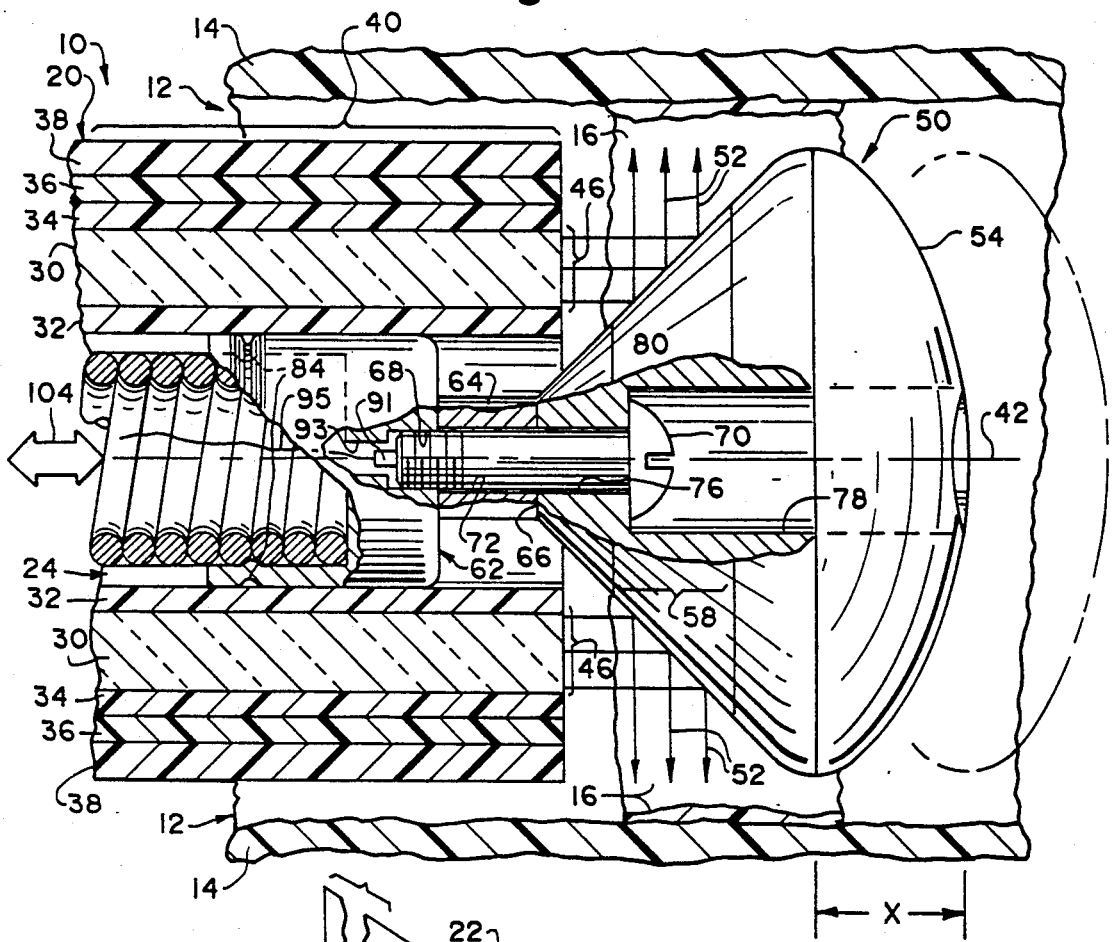
FIG. 1 is a fragmentary, side elevational view, partly in section, showing the distal end portion of a catheter embodying the present invention and received within a body cavity.

Referring now to FIG. 1, a medical device in the form of a catheter 10 embodying the present invention is shown positioned within a body cavity 12. The catheter may be inserted, if desired, through an endoscope, cannula, or other surgical tool (not illustrated). The cavity 12 may be a natural or surgically created cavity or passage in body tissue 14. For example, the tissue 14 may define a blood vessel or duct, or other cavity in an organ.

A portion of the cavity 12 may be characterized as defining a body site containing a material 16 which is to be altered by application of laser radiant energy. The material 16 may be a part of the tissue 14 per se or may be an altered form of the tissue 14, such as cancerous tissue. The material 16 could also be an additional deposit on the tissue 14. For example, such a deposit may be a clot, fat, or arteriosclerotic plaque.

The catheter 10 of the present invention is especially suitable for use in a body cavity in which the material 16 to be altered by the radiation extends generally circumferentially around the interior of the cavity in a substantially 360° circumferential configuration. The catheter 10 is adapted to direct a 360° beam of radiation toward the surrounding material 16.

The catheter 10 includes a length of a hollow, optical fiber 20 which functions as an elongated, laser energy transmitting conduit. Laser energy may be supplied to the hollow fiber 20 in a suitable manner. In one contemplated preferred embodiment illustrated in FIG. 2, at least one conventional, flexible, solid core optical fiber 21 couples the proximal end of the hollow fiber 20 to a laser energy source or system indicated generally by reference numeral 22. The system 22 generates and supplies radiant laser energy (i.e., radiation) to the fiber 21 which in turn transmits the radiation into the hollow fiber 20.

The terms "laser energy", "laser radiation", "laser beam" and variants thereof as used in this specification disclosure and in the claims will be understood to encompass a broad range of radiation frequencies, characteristics, and energy densities. The laser radiation may be suitably produced by a conventional laser such as, for example, a laser of the neodymium:yttrium aluminum garnet (Nd:YAG) type. Other laser types may include carbon dioxide, argon, holmium:yttrium aluminum garnet (holmium:YAG), and excimer. Radiation that may be used in various applications can include infrared radiation (IR), ultraviolet radiation (UV), and visible light.

The system 22 includes conventional means for injecting the radiant laser energy into the optic fiber 21 so that the energy will be transmitted along the fiber 21, and this constitutes a coupling system between the focused radiant energy laser beam and the optic fiber 21. The design, construction, and operation of laser sources and coupling systems are well known in the art and are not described in detail herein. The details of the design, construction, and operation of such laser sources and coupling systems form no part of the present invention.

The fiber 20 is a conventional, single, solid elongate, unitary optical fiber having a core which may be made of glass or silica quartz and which is covered with a thin cladding (not illustrated). The fiber core terminates in a transverse, substantially flat, circular, uncovered, energy delivery surface at the distal end. The laser radiation transmitted along the fiber core is emitted from the distal end surface.

In some applications, the fiber 20 may be formed from polymeric materials such as, for example, poly(-methylmethacrylate) or polystyrene. The diameter of the core is preferably between about 300 microns (0.3 mm.) and about 1,000 microns (1 mm.). In one contemplated embodiment of the present invention, the diameter of the core is about 600 microns (0.6 mm.).

Various optical fibers that may be suitable for particular applications are commercially available. For example, a fiber optic having a core diameter of 0.4 mm. is marketed under the designation Med 400 by Quartz Products Corporation of Plainfield, N.J. A 0.6 mm. diameter fiber optic is commercially available under the designation HCT 600 from Ensign Bickford Co., Connecticut.

The power that can be transmitted along optical fiber varies with the size of the fiber. Utilizing the above-described HCT 600 fiber optic, a medical device embodying this invention can transmit as much as about 60 watts continuous power from a Nd:YAG laser source.

The thin cladding material has a refractive index which differs from the refractive index of the fiber core. The material employed for the core outer cladding is selected on the basis of the refractive indexes relative to the core refractive index such that the laser radiation is confined within the fiber core with a minimum attenuation.

Finally, in some applications it may be desirable to include an outer tubular covering over the cladding. The covering may be a synthetic resin polymer such as the polymer sold under the trademark TEFLON. Other materials that may be used for the cover include silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations of these.

The fiber 20 is a single, hollow, elongate, unitary optic fiber. It has a generally tubular configuration. The transverse cross section is ring-shaped, and, as illustrated in FIG. 1, a central, generally cylindrical channel 24 extends the length of the fiber 20. A hollow optic fiber construction which may be employed in the present invention is disclosed in U.S. Pat. No. 4,768,858.

The fiber 20 in the present invention has an annular core 30 which may be made of glass or silica quartz. Alternatively, in some applications, the fiber 20 may be formed from plastic materials such as, for example, methyl methacrylate or polystyrene. In one contemplated embodiment of the present invention, the inner diameter of the core 30 is about 1.5 mm., and the outer diameter of the core 30 is about 2.5 mm.

In a preferred embodiment, an inner cladding 32 is disposed to cover the inner cylindrical surface of the fiber core 30, and an outer cladding 34 is disposed to cover the outer cylindrical surface of the core 30. The same material may advantageously be used for both the inner cladding 32 and the outer cladding 34.

The cladding material has a refractive index which differs from the refractive index of the fiber core 30. The materials employed for the core inner cladding 32 and outer cladding 34 are selected on the basis of the refractive indexes relative to the core refractive index such that the laser radiation is confined within the fiber core 30 with a minimum attenuation. It is desirable in many applications that the internal reflection caused by the cladding 32 and 34 be such that the radiation emitted from the end of the fiber core 30 has a relatively low divergence.

Examples of suitable cladding materials include silicone, silica, air, or plastic. Plastic material suitable for cladding includes poly(methylmethacrylate) or a mixture of poly(methylmethacrylate) and polystyrene. In a contemplated embodiment, the cladding 32 and 34 is silicone. If the cladding is a solid, the inner cladding and outer cladding each may have a thickness that is preferably in the range of about 0.06 mm. to about 0.1 mm.

Although not necessary in all applications, a sheath 36 may be disposed around the outer cladding 34. The sheath 36 may be, for example, polyethylene.

Also, in some applications it may be desirable to include an outer tubular covering 38, instead of, or in addition to, the sheath 36. The covering 38 may be a synthetic resin polymer such as the polymer sold under the trademark TEFLON. Other materials that may be used for the cover 38 include silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations of these.

If desired, sections of the wall of the catheter may be reinforced. Further, radiopacity can be obtained by incorporating lead or barium salts into the wall of the catheter.

In any event, any exterior surfaces of the catheter which are intended to contact body tissues should preferably be of a material which is biocompatible for the time period during which the catheter will be received within the body cavity.

In a contemplated preferred embodiment, the hollow optical fiber 20 has an annular radiation-transmitting core with an inside diameter of about 1.5 mm. and an outside diameter of about 2.5 mm. The fiber 20 is provided in the form of a relatively inflexible, short segment having a length of between about 50 mm. and about 30 mm. as defined between two parallel, flat, annular end faces. The short segment of the annular optical fiber 20 is coupled to the laser through the relatively long and flexible, single, conventional, solid core, cylindrical, optical fiber 21 which preferably has a diameter of between about 0.3 mm. and about 1 mm., for example, 0.6 mm.

The solid fiber 21 is coupled at one end to the laser and is disposed with its other end adjacent an end of the short length of annular optical fiber (as taught by, for example, U.S. Pat. No. 4,465,335 with reference to solid optical fiber 22 and annular optical fiber 14 in FIG. 1). The end of the solid fiber 21 that is adjacent the annular fiber has a flat, circular end face which confronts, and which is approximately parallel to, a portion of the annular face on the proximal end of the annular optical fiber. The laser radiation is emitted from the solid fiber 21 and passes into the proximal end of the annular fiber 20. The radiation is distributed around the annular fiber 20 and is emitted at the distal end annular face as a generally ring-like beam.

If desired, the length of the solid optical fiber 21 between the laser source 22 and the hollow fiber 20 may be enclosed with a suitable, preferably flexible, tube or covering 39.

The catheter 10 has a distal end region 40 that extends along a longitudinal axis 42 and that terminates in a transverse, substantially flat, annular, energy delivery surface 46. The laser radiation transmitted along the fiber core 30 is emitted from the surface 46.

A reflector means, such as a mirror member or block 50, is positioned axially adjacent the energy delivery surface 46 for intercepting and reflecting the emitted radiation in a beam that radiates outwardly, around the axis. At least a portion of the beam is radiated substantially transversely of, and substantially 360° around, the axis 42 as schematically indicated by the arrows 52.

The mirror block 50 has a rounded front end 54 which is smooth and which is adapted to gently slide past body tissue in the cavity 12 with a minimum of trauma to the tissue. Preferably, at least the rounded front surface 54 is coated with a non-stick or release coating such as polytetrafluoroethylene to provide easy release from tissue.

The reflector block 50 has a generally conical end that includes a frustoconical reflecting surface 58 which is defined around a central axis that is coincident with the longitudinal axis 42. The frustoconical surface 58 is oriented to diverge away from the axis 42 with increasing distance from the fiber distal end region 40.

The frustoconical reflecting surface 58 may be provided by a reflective layer of suitable material that is effective with the wavelength of the particular laser radiation. Examples of suitable materials include platinum, silver, copper, or gold. For example, a conventional gold plating that is commercially available is one marketed under the designation LASER GOLD by Epner Technology, Inc., 25 Division Place, Brooklyn, N.Y. 11222, U.S.A.

The reflecting coating is applied to a generally solid mass of material forming the reflector block 50. Preferably, the reflector block is made of metal, such as surgical stainless steel or copper, but could also be made of a combination of thermally conductive and thermally insulating materials such as metals and ceramics. The mass of metal forming the block 50 functions as a heat sink for the small portion of the radiation energy which is absorbed and converted into heat at the reflecting surface 58.

In some applications, the reflector block 50 may be made from non-metallic materials, such as glass, diamond, or sapphire. Fused silica and glass sold under the trademark PYREX are preferred because of their high thermal shock resistance and relatively lower cost compared to diamond and sapphire. The reflective surface 58 may be provided on the glass in the form of a metallic film of dielectric. Metallic coatings can include aluminum, gold, silver, copper, platinum, and rhodium. A film of silicon monoxide or magnesium fluoride can be deposited over the metal for protection. A dielectric coating can be prepared by vacuum-deposition on the glass of alternate layers of magnesium fluoride and cerium dioxide films. The coating material and thickness depend on the angle of the reflecting surface 58 and on the wave length of the incident laser radiation.

Preferably, the angle of the frustoconical reflecting surface, relative to the longitudinal axis 42, is about 45°. Most of the laser radiation (which is preferably emitted from the annular surface 46 in a ring beam around the axis 42 with little or no substantial divergence) will then be reflected outwardly, around the axis 42. At least a portion of the beam is radiated substantially transversely of, and substantially 360° around, the axis 42. The reflected radiation 52 is thus laterally directed to the target material 16 at the body cavity site.

The reflector block 50 is mounted to a cylindrical sleeve 62 which is slidably disposed within the central channel 24 in the fiber core 30. The reflector block 50 is spaced from a closed forward end of the sleeve 62 by a generally cylindrical spacer 64. The reflector block 50 has a reduced diameter end surface 66 which mates against the end of the spacer block 64.

The end of the sleeve 62 has a threaded bore 68 for receiving a machine screw 70. The spacer 64 defines a bore 72 for receiving a portion of the length of the shank of the machine screw 70. Similarly, a portion of the reflector block 50 defines a bore 76 for receiving a portion of the screw shank. The block 50 further defines a counterbore 78 which terminates at an annular shoulder 80 for receiving the head of the machine screw 70.

The sleeve 62 is open at one end to receive an end of an elongate drive means, such as a flexible drive cable 82. The cable 82 may be a conventional torque cable comprising a helically wound wire. The sleeve 62 is crimped into engagement with the cable 82 at 84.

The cable 82 extends along the entire length of the fiber core central channel 24 and beyond to the proximal end of the catheter device. The rear end of the cable 82 is received in a sleeve 86 which is crimped to the cable 82 at 88. The cable 82 and sleeve 86 are slidably disposed on a guide rod 90 carried by a frame 91 on which the laser source and coupling system 22 may be mounted.

A rack gear 92 is fixed to the side of the sleeve 86 and is engaged with a pinion gear 94. The pinion gear 94 is mounted to a shaft 96 along with a thumb-operable drive wheel 98. The shaft 96 is mounted for rotation in a bracket 100 on the frame 91. Rotation of the thumb wheel 98 will effect movement of the sleeve 86 and hence, of the cable 82, along the longitudinal axis in either of the directions indicated by the double headed arrows 104.

The cable 82 functions as an actuator means for effecting axial movement of the reflector block 50 along the longitudinal axis 42 for a distance X or more as illustrated in FIG. 1. The block 50 can be located at selected axial positions along the axis when the distal end of the catheter 10 is maintained stationary in the vicinity of the selected body cavity site. The 360° radiation beam can be axially moved along the body site to irradiate the target material 16 without requiring further movement of the entire catheter 10. This minimizes the potential for tissue trauma.

If desired, the cable 82 and gear drive mechanism may be replaced with other suitable actuator systems. For example, a simpler system could include a manually operated plunger or rod.

Typically, according to the method of the present invention, the catheter 10 is advanced to the vicinity of the body cavity site with the reflector block 50 positioned at a selected axial location along the axis 42 so as to be able to irradiate the body site.

As previously explained, in some treatment procedures the catheter is preferably advanced through an endoscope, cannula, or other surgical tool to the body site. Fluids may be pumped through the endoscope, cannula, or other surgical tool and infused about the catheter. Such fluids can include flushing fluids or treatment fluids, such as saline, glycine, sterile water, gases (such as carbon dioxide), and oxygen bearing liquids. Drugs, such as an anti-coagulant, anti-spasmodic, anti-vasoconstrictive, or others, can be infused along with a flushing fluid. A radiopaque liquid can also be introduced for fluoroscopic viewing. In some cases, the fluid may be a heat transfer agent for use in heating or cooling the catheter components or body site. The fluid may be directed against the reflector block 50. Also, suction could be effected through the endoscope (or other tool).

Laser radiation is then transmitted through the fiber 20. The emitted radiation is intercepted and reflected transversely of, and substantially around, the longitudinal axis 42. The block 50 is moved to selected axial positions along the axis 42 to irradiate the entire body site. In one contemplated mode of operation, the reflecting block 50 would be moved continuously from a position closest to the energy delivery surface 46 to a position furthest from the energy delivery surface 46 so as to move the 360° beam along a selected segment of the cavity wall 14.

In some applications, it may be desired to provide a means for sensing the thermal energy of the reflector block 50. For example, in some applications, the temperature of the reflector block 50 should not be allowed increase too high above the ambient temperature. Material or materials used for fabrication of the reflector block 50 may dictate that the temperature increase be limited. Also, it may be desirable to limit the temperature of the reflector block 50 if the body site tissues are in contact with the reflector block 50 during the irradiation procedure. To this end, a thermocouple or other temperature sensing device may be provided in the catheter 10. In particular, FIG. 1 illustrates how a thermocouple junction 91 can be attached to the end of the shank of the screw 70 within a bore 93 that is defined within the sleeve 62. The junction 91 may be secured to the screw 70 with a suitable adhesive or epoxy (not illustrated).

The lead wires or cable 95 can be routed from the junction 91 through the bore 93, along the central channel 24 defined in the fiber 20, and to the laser source system 22.

Preferably, the thermocouple is provided as part of a control system (not illustrated) which operates an appropriate annunciator or alarm system when a predetermined set point temperature is reached. The control system may also operate to reduce the laser energy output or to completely terminate the operation of the laser. Such a temperature sensing control system is advantageously used where fluid flow is provided through the catheter to the reflector block 50 for purposes of cooling. In such cases, the temperature could increase if the laser is operated for too long a time period or if the cooling flow is obstructed (e.g., by tissue adherence to the reflector block 50). Such a temperature sensing and control system can effectively operate to prevent deterioration or destruction in those situations where excessive heat is absorbed by the reflector block 50.

An alternate embodiment of the present invention is illustrated in FIG. 3 wherein a modified form of the catheter is designated generally by the reference numeral 210. The catheter 210 includes an optic fiber 220 having an annular fiber optic core 230, inner cladding 232, outer cladding 234, a sheath 236, and a covering tube 238. The sheath 236 and/or covering tube 238 may be eliminated in some applications. The construction and materials of the core, cladding, sheath, and covering may be the same as described above for the first embodiment of the catheter 10.

The fiber 220 has a distal end region 240 that extends along a longitudinal axis 242. The fiber core 230 terminates at a transverse, substantially flat, annular, energy delivery surface 246 from which the laser radiation is emitted. The fiber 220 is adapted to be connected to a laser source and coupling system, such as the system 22 shown in FIG. 2 and described above with respect to the first embodiment of the catheter 10.

The catheter 210 includes a cap 247 at the distal end of the fiber 220. The cap 247 has a rounded front surface 248 for minimizing trauma to the body tissue and has a cylindrical side skirt 249 which is mounted to, and sealed to, the fiber 220.

Preferably, the sheath 236 and outer covering 238 terminate short of the distal ends of the fiber core 230, inner cladding 232, and outer cladding 234. This forms a shoulder for receiving the skirt 249 which can be adhesively secured to the outer surface of the outer cladding 234 and to the annular ends of the sheet 236 and outer covering 238.

The cap 247 may be made from artificial or natural sapphire, quartz, diamond, polymeric materials, or other materials translucent to laser energy. The cap 247 may be coated with an anti-reflection material. This can include a vacuum-deposited film of magnesium fluoride. The film may have a thickness equal to about ¼ of wavelength of the laser radiation.

The cap 247 isolates the end of the optic fiber 220 from the ambient environment and defines a space at the distal end of the optic fiber 220 which has a predetermined index of refraction. Disposed within the cap 247 is a reflector means in the form of a reflector block 250. The block 250 is formed from a laser transmissible material through which the radiation can be transmitted. The block 250 functions as a prism reflector, and may be made of fused silica, sapphire, glass, crown glass, diamond, zinc selenide, yttrium aluminum garnet, or other suitable materials.

The block 250 has a cylindrical side surface 251 defined between a first end 253 and second end 255. The first end 253 faces the annular energy delivery surface 246. The first end 253 has a generally flat, circular, end surface that is substantially parallel to energy delivery surface 246.

The second end 255 of the block 250 has a recess defined by a frustoconical surface 258 having a central axis which is coincident with the catheter longitudinal axis 242. The laser radiation transmitted along the fiber 220 exits from the fiber at the energy delivery surface 246, enters the block 250 at the first end 253, and impinges upon the frustoconical surface 258.

For the wavelength of the particular laser radiation transmitted, the material of the block 250 is selected so that its index of refraction is greater than the index of refraction of the space within the cap 247 adjacent the reflecting surface 258. Further, the material of the block is selected so that when the frustoconical surface 258 is oriented at an angle of about 45° relative to the longitudinal axis 242, the angle of incidence of the radiation parallel to the axis 242 is equal to, or exceeds, the critical angle (which critical angle is determined, of course, by the indices of refraction of the material of the block 250 and of the space within the cap 247 adjacent the reflecting surface 258—for the wavelength of the particular laser radiation). The incident radiation will thus be substantially totally internally reflected at the surface 258 and will be reflected substantially transversely of, and around, the longitudinal axis 242 as indicated schematically by the arrow 252.

The reflector block 250 is mounted within the cap 247 for axial movement relative to the annular, radiation-emitting surface 246 of the fiber core 230. The block 250 is spaced from the end of a closed sleeve 262 by a cylindrical spacer 264 and is secured to the sleeve 262 with a suitable adhesive or by other appropriate means.

The sleeve 262 is slidably disposed within the central passage of the fiber 220 and is crimped to an end of a drive cable 282 in the passage. The drive cable 282 extends the length of the fiber 220. As illustrated by the double headed arrow 204 in FIG. 3, the drive cable 282 may be reciprocated within the fiber 220 by appropriate means so as to move the reflector block 250 axially along the longitudinal axis 242 for a distance X or greater. Such means for moving the cable 282 may include the gear drive mechanism described above for the first embodiment of the catheter as illustrated in FIG. 2.

Figure 2:
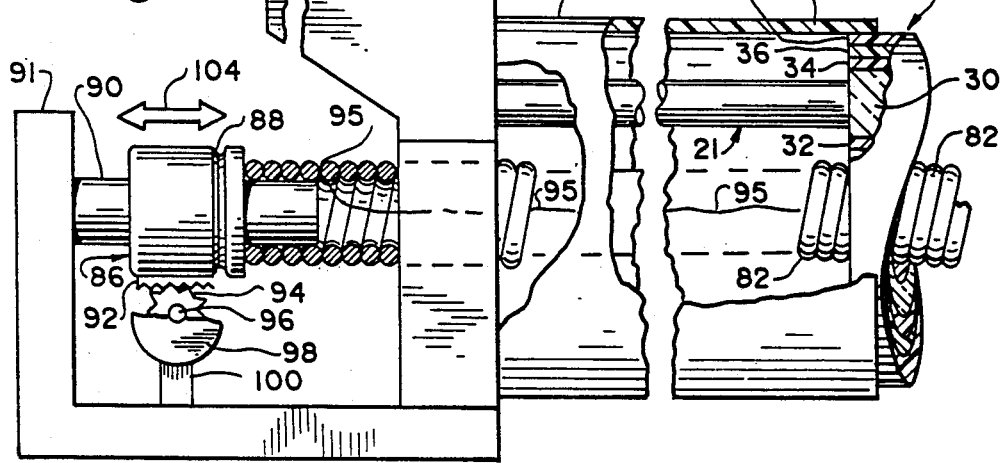
FIG. 2 is a simplified, side elevational view, partly in cross section, of the proximal end portion of the catheter and of the external, remote control system for the catheter.

A thermocouple system may also be provided in the catheter 210 in a manner somewhat similar to that discussed above with respect to the first embodiment of the catheter illustrated in FIG. 1 and 2. In particular, a bore 293 is provided in the sleeve 262 and spacer 264 for receiving a thermocouple junction 291. The junction is secured, as with adhesive, for example, to the spacer 264 at the bottom of the bore 293. The thermocouple lead wires or cable 295 can be run out of the bore 293 to a suitable monitoring or control system.

The first and second embodiments of the catheter may be modified in a variety of ways. For example, a cap, such as the cap 247, may also be employed with the first embodiment of the catheter 10 described above with reference to FIGS. 1 and 2.

It will be appreciated that the present invention provides a novel method for efficiently directing radiation laterally to a body cavity site with a minimum of trauma to the body tissues.

The apparatus which may be employed to carry out the method does not require a complex design incorporating a plurality of optic fibers. Nevertheless, the apparatus permits relatively precise control of the radiation beam. The method and apparatus accommodate the continuous movement of a radiation beam along a length or segment of a body cavity site in an efficient manner.

In accordance with the preceding discussion, further adaptations and variations of the present invention will be readily perceived by a practitioner of the medical instrumentation of arts. Therefore, the present invention should be interpreted in accordance with the language of the following claims and not solely in accordance with the particular embodiments within which the invention has been taught.

What is claimed is:

1. A catheter suitable for coupling to a laser source to direct radiant energy laterally to a selected body cavity site, said catheter comprising:

(a) a hollow, elongate, flexible, optical fiber adapted for coupling to said laser source, said fiber defining a central opening having a circular transverse cross section and having a distal end region that extends along a longitudinal axis and that terminates in a transverse, substantially flat, annular, energy delivery surface for emitting laser radiation transmitted by the fiber;

(b) reflector means positioned axially adjacent said energy delivery surface for intercepting and reflecting said emitted radiation in a beam with at least a portion of said beam radiating substantially transversely of, and substantially around, said axis;

(c) a cylindrical sleeve slidably disposed in said central opening of said fiber and connected to said reflector means; and (d) a flexible drive cable disposed in said central opening of said fiber and connected to said sleeve whereby linear displacement of said drive cable relative to said fiber can be effected to locate said reflector means at selected axial positions along said axis relative to said energy delivery surface whereby said beam irradiates a selected body site along said axis.

2. A catheter in accordance with claim 1 in which said reflector means includes a member having a rounded front surface and frustoconical rear surface defined around a central axis that is coincident with said longitudinal axis of said fiber distal end region; and said frustoconical rear surface is oriented to diverge away from said central axis with increasing distance from said fiber distal end region.

3. The catheter in accordance with claim 1 in which said reflector means includes a block of laser energy transmissible material of a composition through which said radiation can be transmitted;

said reflector means block has a cylindrical side surface defined between first and second ends around a central axis that is coincident with said longitudinal axis of said fiber distal end region;

said first end faces said energy delivery surface of said fiber and defines a generally flat, circular, end surface substantially parallel to said energy delivery surface;

said second end has a recess defined by a frustoconical surface around said central axis at a selected angle; and said catheter further includes a cap through which said radiation can pass and that is sealed around said fiber, that is spaced from said frustoconical surface, and that defines a space between said frustoconical surface and said cap, said space and said reflector means block having predetermined indices of refraction whereby said radiation emitted from said fiber energy delivery surface passes into said reflector means block wherein it is internally reflected by said frustoconical side surface and passes out of said block, through said cylindrical side surface, and through said cap to said body site.

4. The catheter in accordance with claim 1 in which said reflector means includes a metallic coating defining a reflecting surface.

* * * * *